United States Patent
Sato (10) Patent No.: US 7,427,604 B2
(45) Date of Patent: Sep. 23, 2008

(54) **DNA ENCODING AN ANTIGENIC PROTEIN OF *EIMERIA* APICAL MEMBRANE ANTIGEN 1 AND USE THEREOF**

(75) Inventor: Takanori Sato, Tokyo (JP)

(73) Assignee: Zeon Corporation, Tokyo (JP)

( * ) Notice: Subject to any disclaimer, the term of this patent is extended or adjusted under 35 U.S.C. 154(b) by 0 days.

(21) Appl. No.: 11/290,422

(22) Filed: Jan. 20, 2006

(65) Prior Publication Data

US 2006/0115498 A1 Jun. 1, 2006

(30) Foreign Application Priority Data

Dec. 1, 2004 (JP) ............................. 2004-348669

(51) Int. Cl.
*A61K 31/711* (2006.01)
*C07H 21/04* (2006.01)

(52) U.S. Cl. ...................................... 514/44; 536/23.7

(58) Field of Classification Search ....................... None
See application file for complete search history.

(56) References Cited

U.S. PATENT DOCUMENTS

| | | | |
|---|---|---|---|
| 5,028,694 A | 7/1991 | Mewman et al. ............ | 530/350 |
| 5,122,471 A | 6/1992 | Jenkins et al. ............ | 435/252.3 |
| 5,279,960 A | 1/1994 | Anderson et al. ........... | 435/243 |
| 5,387,414 A | 2/1995 | Harwood et al. ......... | 424/191.1 |
| 5,403,581 A | 4/1995 | Binger et al. ............ | 424/191.1 |
| 5,449,768 A | 9/1995 | Chakraborty et al. ..... | 536/24.32 |
| 5,602,033 A | 2/1997 | Vermeulen et al. ..... | 435/252.33 |
| 5,661,015 A | 8/1997 | Binger et al. ............ | 435/172.3 |
| 5,814,320 A | 9/1998 | Clarke et al. ............. | 424/267.1 |
| 6,001,363 A | 12/1999 | Tomley et al. ............ | 424/191.1 |
| 6,248,329 B1 * | 6/2001 | Chandrashekar et al. . | 424/191.1 |
| 6,764,684 B2 | 7/2004 | Saitoh et al. ............. | 424/199.1 |

OTHER PUBLICATIONS

Lodish et al., Mol. Cell Biol., 3rd ed. Scientific American Books, NY, 1995. p. 115.*
Ellis, Vaccines, Plistkin, et al. (eds) WB Saunders, Philadelphia, 1998, p. 568-575.*
Oshop et al., Vet. Immunol. Immunopathol., 89:1-12, 2002.*
Li et al., Genome Res., 13:443-454, 2003.*
Shirley et al. (Adv. Parasitol., 60:285-330, 2005.*
Greenspan et al., Nature Biotechnology 7: 936-937, 1999.*
Bowie et al., Science, 1990, 257:1306-1310.*
XP002040617; Karkhanis et al; "Purification and Characterization of a Protective Antigen . . . ;" Infection and Immunity, Mar. 1991, pp. 983-989.
XP000197593; Bhogal et al; "Potential of a recombinant antigen as a prophylactic vaccine for day-old boiler chickens against *Eimeria acervulina* and *Eimeria tenella* infections;" Veterinary Immunology and Immunopathology, 31(1992) pp. 323-335.
XP002372983; Binger et al; "Cloning and characterization of a surface antigen of *Eimeria tenella* merozoites and . . . ;" Molecular and Biochemical Parasitology, 61 (1993) pp. 179-188.
XP000676512; Talebi et al; "High-Resolution Mapping of B-Cell Epitopes within an Antigenic Sequence from *Eimeria tenella*;" Infection and Immunity, Oct. 1994, pp. 4202-4207.
XP002372984; Pogonka et al; "A single dose of recombinant *Salmonella typhimurium* induces specific humoral immune responses against heterologous . . . ;" International J. Parasitology, 33 (2003) pp. 81-88.
XP004458016; Guzman et al; "A comparison between IgG antibodies against *Eimeria acervulina E. Maxima*, . . . vaccinated with live anticoccidial vaccines;" Vaccine 21 (2003), pp. 4225-4233.
Hehl, Adrian B., et al; "Toxoplasma gondii Homologue of Plasmodium Apical Membrane Antigen 1 is Involved in Invasion of Host Cells;" Infection and Immunity, (Dec. 2000) pp. 7078-7086.
European Search Report dated Mar. 3, 2006.
Lalitha et al; "Production of the Subdomains of the Plasmodium falciparum Apical Membrane Antigen 1 Ectodomain and Analysis of the Immune Response;" Infection and Immunity (Aug. 2004), vol. 72 No. 8; pp. 4464-4470.
Pan et al; "Fusion of Two Malaria Vaccine Candidate Antigens Enhances Product Yield, Immunogenicity, and Antibody-Mediated Inhibition of Parasite Growth In Vitro;" J. Immun. (2004), 172:6167-6174.
Healer et al; "Allelic polymorphisms in apical membrane antigen-1 are responsible for evasion of antibody-mediated inhibition in Plasmodium falciparum;" Molecular Microbiology (2004) 52(1), 159-168.
Jenkins et al; "*Eimeria acervulina*: DNA Cloning and Characterization of Recombinant Sporozoite and Merozoite Antigens;" Experimental Parasitology (1988) 66, 96-107.
Jeffers; "Attenuation of *Eimeria tenella* Through Selection for Precociousness;" J. Parasitology (Dec. 1975) vol. 61, No. 6, pp. 1083-1090.

* cited by examiner

Primary Examiner—Shanon A. Foley
Assistant Examiner—Brian J Gangle
(74) Attorney, Agent, or Firm—Kratz, Quintos & Hanson, LLP (57) ABSTRACT

This invention provides a novel DNA for preventing avian coccidiosis and use thereof. The novel DNA encodes an antigenic protein of *Eimeria* apical membrane antigen 1, and is used for DNA vaccine and/or for vaccine comprising the recombinant protein deduced from the said DNA sequence as a main ingredient. The chickens immunized with vaccines described herein can be induced immunity against coccidiosis.

6 Claims, 6 Drawing Sheets

```
                                                        Reading  High   Probability
     Sequences producing High-scoring Segment Pairs:    Frame    Score  P(N)       N
     EMBL:BG516125  EtESTed49e08.y1 Eimeria tenella S5-2 cD...  +1   202   2.0e-16   1
     EMBL:BG725003  EtESTed44d06.y1 Eimeria tenella S5-2 cD...  +1   178   9.0e-14   1
     EMBL:BG724708  EtESTed87d05.y1 Eimeria tenella S5-2 cD...  +3   113   1.1e-10   2
     EMBL:AI759570  EtESTea22c10.x1 Eimeria S5-2 Sporozoite...  -1    67   0.24      1
     EMBL:BM321931  EtESTee19c06.y1 Eimeria tenella M5-6 cD...  +2    76   0.43      1
     EMBL:BG561244  EtESTed82e07.y1 Eimeria tenella S5-2 cD...  +1    76   0.49      1
     EMBL:BM322018  EtESTee20g07.y1 Eimeria tenella M5-6 cD...  -2    70   0.98      1
```

(B)

```
BG725003   1    ---------- ---------- ---------- ---------- ---------- ----------
BG724708   1    AGACACCCGG CGGCACTGCA GCAGCAGCAG CTGGCGTGGC CCTTCTGCAG CAGTTGCGGT

BG725003   1    ---------- ---------- ---------- -TCAAAATTT GAAAAAAAGA AATCCCAAAA
BG724708  61    CTCTTGATAT TCCATTCGAG TTTGATTTTA CTCAAAATTT GAAAAAAAGA AATCCCAAAA

BG725003  30    CTTGAAAAGA CCCCCCAGCA CCATGCGGCG GCTTTCCCCA GCTCTGGGCC TTCTTGCTGC
BG724708 121    CTTGAAAAGA CCCCCCAGCA CCATGCGGCG GCTTTCCCCA GCTCTGGGCC TTCTTGCTGC

BG725003  90    GGCCCTCAGC TGCGCAGGGC CGGCAGCAGG GGTGCAGCAC AAGCTGCAGC ACAGGCAGCA
BG724708 181    GGCCCTCAGC TGCGCAGGGC CGGCAGCAGG GGTGCAGCAC AAGCTGCAGC ACAGGCAGCA

BG725003 150    GCAGCAGCAG CAGCACAGCC ACGCCTCAAC TTCGCATGCT GCTGCAGTTC TTGCTGCTTC
BG724708 241    GCAGCAGCAG CAGCACAGCC ACGCCTCAAC TTCGCATGCT GCTGCAGTTC TTGCTGCTTC

BG725003 210    TTCGGATGCA TCCACAGACT CCAATCCCTT CATGCAGCCG CCCTATGCCG AGTTCATGGC
BG724708 301    TTCGGATGCA TCCACAGACT CCAATCCCTT CATGCAGCCG CCCTATGCCG AGTTCATGGC

BG725003 270    CAGATTCAAC ATTCCCAAAG TCCACGGGAG CGGGG-TGTA CGTGGACCTG GGGAACGACA
BG724708 361    CAGATTCAAC ATTCCCAAAG TCCACGGGAG CGGGGNTGTA CGTGGACCTG GGGAACGACA

BG725003 329    AAGAGGTGAA GGGAAAGATG TACAGAGAGC CTGGGGGCCG CTGTCCCGTC TTTGGCAAAA
BG724708 421    AAGAGGTGAA GGGAAAGATG TACAGAGAGC CTGGGGGCCG CTGTCCCGTC TTTGGCAAAA

BG725003 389    ACATCGAGTT TTATCAGCCC CTGGATTCGG ACTTGTACAA AAACGACTTT CTCGAAAATG
BG724708 481    ACATCG---- ---------- ---------- ---------- ---------- ----------

BG725003 449    TCCCGACGGA AGAAGCAGCA GCAGCAGCAA AGCCCCTCCC CGGAGGCTTC AACAACAACT
BG724708 486    ---------- ---------- ---------- ---------- ---------- ----------

BG725003 509    TTTTG
BG724708 486    -----
```

```
TgAMA1:         157  IKASTDLGRCAEFAFKTVAMDKNNKATKYRYPFVYDSKKRLCHILYVSMQLMEGKKYCSV  216
                     +KA T LG+CAE ++ T A   + YRYPFV+DSKK LC++L V +Q + G++YCS
c001002545.Contig1:  93  KARTGLGKCAEMSYLTTAA------GSSYRYPFVFDSKKDLCYLLLVPLQRLMGERYCST  146

TgAMA1:         217  KGEPPDLTWYCFKPRKSVTENHHL  240
                     +G PP L + +CFKP KSV+    HL
c001002545.Contig1:  147  RGSPPGLSHFCFKPLKSVSLRPHL  170
```

(B)

```
TgAMA1:         241  IYGSAYVGENPDAFISKC  258
                     +YGSAYVGE PD + +KC
c001002545.Contig1:  171  VYGSAYVGERPDDWETKC  188
```

(C)

```
TgAMA1:         260  NQALRGYRFGVWKKGRC  276
                     N+A++   FGVW+ GRC
c001002545.Contig1:  189  NKAVKDAVFGVWEGGRC  205
```

(D)

```
TgAMA1:         336  SGGVGRNYGFYYVDTTGEGKCALSDQVPDCLVSDSAAVSYTAAGSLSEETPNFIIPSNPS  395
                     ++GVG N+ YY       G+C LS +VP CL+  A ++T+ GSL EE     P+ P+
c008400755.Contig1:  1    GVGVNFASYYPS------GECVLSGEVPTCLLPRQGAAAFTSVGSLEEEELPHCDPTFPA  54
```

Sequences producing significant alignments: (bits) Value
AF010264_1(AF010264|pid:g2293476) Toxoplasma gondii apical memb... 339  9e-92
PCU49743_1(U49743|pid:g1469496) Plasmodium chabaudi DS apical m... 148  3e-34

(B)

AF010264_1(AF010264|pid:g2293476) Toxoplasma gondii apical membrane antigen 1 homolog (AMA1Tg)
Length = 541
Score = 339 bits (861), Expect = 9e-92
Identities = 192/485 (39%), Positives = 255/485 (52%), Gaps = 37/485 (7%)

```
EtAMA1:  61 NPFM-QPPYAEFMAGFNIPKVHGSGVYVDLGNDKEVKGKMYREPGGRCPVFGKNIEFYQP 119
            NPF     FM FN+   H SG+YVDLG DKEV G +YREP G CP++GK+IE  QP
TgAMA1:  42 NPFQANVEMKTFMERFNLTHHHQSGIYVDLGQDKEVDGTLYREPAGLCPIWGKHIELQQP 101

EtAMA1: 120 LDSDLYKNDFLENVPTE-EAAAAAKPLPGGFNNNFLMKDKKPFSPMSVAQLNSYPQLKAR 178
              D  Y+N+FLE+VPTE E     +  PLPGGFN NF+   +  SP + L    +KA
TgAMA1: 102 -DRLPYRNNFLEDVPTEKEYKQSGNPLPGGFNLNFVTPSGQRISPFPMELLEKNSNIKAS 160

EtAMA1: 179 TGLGKCAEMSYLTTA------AGSSYRYPFVFGSKKDLCYLLLVPLQRLMGERYCSTRGSP 233
            T LG+CAE ++ T A      + YRYPFV+ SKK LC++L V +Q + G++YCS +G P
TgAMA1: 161 TDLGRCAEFAFKTVAMDKNNKATKYRYPFVYDSKKRLCHILYVSMQLMEGKKYCSVKGEP 220

EtAMA1: 234 PGLSHFCFKPLKSVSLRPHLVYGSAYVGERPDDWETKCPNKAVKDAVFGVWEGGRCEEQR 293
            P L+ +CFKP KSV+  HL+YGSAYVGE PD + +KCPN+A++  FGVW+ GRC +
TgAMA1: 221 PDLTWYCFKPRKSVTENHHLIYGSAYVGENPDAFISKCPNQALRGYRFGVWKKGRCLDYT 280

EtAMA1: 294 LRLGAQTAAAAAKEDCWALAFNNPFAASDQP-TSQDEAATSPGYYFPSITPSQPKSGGVG 352
                  K  CW   FN   ASDQP T    + S   ++P     QP SGGVG
TgAMA1: 281 ELTDTVIERVESKAQCWVKTFENDGVASDQPHTYPLTSQASWNDWWPLHQSDQPHSGGVG 340

EtAMA1: 353 VNFASYY------PSGECVLSGEVPTCLLPRQGAAAFTSVGSLEEEELPHCDPT------ 400
             N+  YY       G+C LS +VP CL+  A  +T+ GSL EE    P+
TgAMA1: 341 RNYGFYYVDTTGEGKCALSDQVPDCLVSDSAAVSYTAAGSLSEETPNFIIPSNPSVTPPT 400

EtAMA1: 401 ----------FPASLGSCDPSSCKAILTECRGGRLVEQQTDCVPEDGSKCESKGGGVFI 449
                      FP S G+CD +CK   T C GG++   DC ++ ++C S
TgAMA1: 401 PETALQCTADKFPDSFGACDVQACKRQKTSCVGGQIQSTSVDCTADEQNECGSNTALIAG 460

EtAMA1: 450 GLAVAGGLLLLLLTGGAFFIYKQRQKALPKESSPQRTDFVQDEAATGRGKKRQSDLVQQA 509
               +   +LL+LL+ G F  RK +  +++     +F D  G KKR SDL+Q+A
TgAMA1: 461 LAVGGVLLLALLGGGCYFAKRLDRNKGV--QAAHHEHEFQSDRGAR---KKRPSDLMQEA 515

EtAMA1: 510 EPSFW 514
            EPSFW
TgAMA1: 516 EPSFW 520
```

DNA ENCODING AN ANTIGENIC PROTEIN OF *EIMERIA* APICAL MEMBRANE ANTIGEN 1 AND USE THEREOF

BACKGROUND OF THE INVENTION

1. Field of the Invention

This invention is in the field of avian coccidiosis and is related to a DNA molecule encoding an antigenic protein of *Eimeria* apical membrane antigen 1 and use thereof.

Coccidiosis is an intestinal disorder of poultry and causes an assortment of problems in the infected host. These problems range from poor feed conversion ratios in light infections to acute death in heavier infections.

Coccidiosis is caused by protozoans belonging to the genus *Eimeria*. The members of this genus in poultry are *E. acervulina, E. tenella, E. maxima, E. necatrix, E. brunetti, E. mitis* and *E. praecox*. Some investigators include *E. mivati* and *E. hagani* into the member. All of these species have similar life cycles but display different tissue specificity and pathogenicity. A broiler chicken will be subjected to a great deal of damage by *E. acervulina* or *E. maxima* because they parasitize large portions of the small intestine, where food digestion plays a major role.

Coccidiosis can be controlled by the administration of anti-coccidial agents. However, drug resistant strains arise at a frequent rate and the cost of development of new drugs is quite high. In addition, a number of these agents leave residues in the meat, which might give problems on consumer.

Attempts have been made to prevent the disease by vaccinating chickens with live attenuated strains of *Eimeria* or inactivated parasites. These live attenuated strains such as precocious lines are obtained by inoculating chickens with oocysts of a wild *Eimeria* species and collecting the very first parasite that are excreted as a result of infection (J Parasitol. 1975, 61: 1083-1090). However, such attenuated live vaccines produce fewer parasites and give an appreciable disease effect to vaccinated chickens. On the other hand, a protection level using the latter (inactivated vaccine) is far from complete. Furthermore, the disadvantage of these vaccines is expensive to be produced because a large-scale production of these vaccines needs a lot of live chickens.

An alternative solution would be to produce, by genetic engineering, the protective antigens of *Eimeria* parasites. Once developed, these immunogens could be produced cheaply in a prokaryotic or eukaryotic culture system in an unlimited supply and used to vaccinate chickens against coccidiosis.

2. Related Art

Several protective antigen genes of *Eimeria* have been reported. For examples, Jenkins et al. reported screening using a rabbit serum against the membrane fraction of *E. acervulina*, and a part of the cDNA encoding a 250-kDa protein in parasite surface (Exp. Parasitol. 1988; 66: 96-107, U.S. Pat. No. 5,122,471). Some *Eimeria* antigen genes were screened using monoclonal antibodies to *Eimeria* parasites instead of antisera (U.S. Pat. Nos. 5,028,694, 5,279,960, 5,814,320, 5,449,768). However, these antigens could elicit only partial protection against *Eimeria* infection to chickens immunized with a recombinant protein or recombinant virus expressing the antigen (U.S. Pat. Nos. 5,387,414, 5,403,581, 5,602,033, 6,001,363).

*Plasmodium* that causes human malaria is closely related to *Eimeria*, and both parasites belong to the phylum of Apicomplexa. Malaria is one of three major infection diseases of human, and there are an estimated 500 million infected persons, with 1-2 million dying annually. Therefore, many research teams focus on developing malaria vaccine to control infection. *Plasmodium* apical membrane antigen 1 is currently, one of the most promising antigens for Malaria vaccine (Molecular Microbiology (2004) 52, 159-168, The Journal of Immunology 172 (2004) 6167-6174, and Infect. Immun. 72 (2004) 4464-4470). The *Eimeria* apical membrane antigen 1 (AMA-1) gene is expressed only small amount in the specific organ of *Eimeria*. Therefore the purification of the antigen was difficult, and full amino acid sequence was unknown. Because there was no purified AMA-1, it was difficult to get the AMA-1 gene by the general screening method that is to obtain an antibody against the antigen and to screen a cDNA library with the antibody.

As described above, there is no satisfied vaccine against Avian Coccidiosis. In addition that, a DNA molecule encoding *Eimeria* AMA-1 protein has not been cloned and known in terms of usefulness for vaccine antigen.

SUMMARY OF THE INVENTION

Accordingly, an object of the present invention is to provide a means for identifying and cloning of cDNA encoding *Eimeria* AMA-1. A further object of the present invention is to provide a DNA molecule encoding *Eimeria* AMA-1 and use thereof. Still further objects of the present invention are to provide methods and vaccines useful for protecting chickens against avian coccidiosis.

The present invention provides a DNA molecule encoding an antigenic protein of *Eimeria* AMA-1, specifically *Eimeria tenella* AMA-1. More especially, the DNA sequence encodes the *Eimeria tenella* AMA-1 protein comprising of the amino acid sequence shown in SEQ. ID. No. 2.

Additionally, the present invention provides a DNA molecule encoding an antigenic protein of *Eimeria* AMA-1, wherein the antigenic protein comprises of an amino acid sequence, which is modified by insertion, deletion, and/or substitution of one or more amino acids in the sequence shown in SEQ ID No. 2, or wherein the antigenic protein with more than 90% identity to the amino acid sequence shown in SEQ ID No. 2.

Moreover, the present invention provides a DNA molecule encoding an antigenic protein of *Eimeria* AMA-1, wherein said the DNA molecule is hybridized to the region of open reading frame in the DNA shown in SEQ ID No.1 under high stringent condition.

A DNA vector containing the DNA molecule described above is also disclosed herein, and can be used as DNA vaccine for avian coccidiosis.

The present invention provides an antigenic protein of *Eimeria* AMA-1 and a method of producing it.

The protein is also useful for protecting chickens against Avian coccidiosis.

DETAILED DESCRIPTION OF THE INVENTION

Antigenic Protein of *Eimeria* Apical Membrane Antigen 1

*Eimeria* apical membrane antigen 1 (AMA-1) of the present invention is derived from *Eimeria*, avian parasite, and does, more specifically, comprise the amino acid sequence of SEQ ID No.2.

However, the antigenic protein of *Eimeria* AMA-1 is not limited only to AMA-1, but includes the protein that comprises the amino acid sequence modified by substitution, deletion, addition and/or insertion of one or more amino acids in SEQ ID No.2, so long as it could induce the similar antibodies into chicken as those induced into chicken immunized with *Eimeria* AMA-1. The sample of the said antigenic protein is one having the same epitope as *Eimeria tenella* AMA-1 comprising the amino acid sequence shown in SEQ ID No. 2, and one example is the recombinant protein described in Example 3, which is containing from the 57$^{th}$ to 276$^{th}$ amino acid of SEQ ID. No. 2.

The numbers of the above amino acid modification are preferable, less than 10%, more preferably less than 5% to the whole of SEQ ID No.2, and are most preferably less than 10 amino acids.

The antigenic protein of *Eimeria* AMA-1 of the present invention is also encoded to the DNA molecule that is hybridized to the DNA molecule of the open reading frame in SEQ ID No.1 under high stringent condition. In this case, the high stringent condition is equivalent to "0.2×SSC and 68° C."

Moreover, antigenic proteins of *Eimeria* AMA-1 of the present invention include the protein comprising amino acid sequence that is more than 90% identity to the amino acid sequence shown in SEQ ID No. 2, and being antigenic protein of *Eimeria tenella* AMA-1. Preferably, the identity is more than 95% at least.

DNA Molecule Encoding an Antigenic Protein of *Eimeria* AMA-1

The DNA molecule of the present invention encodes an antigenic protein of the aforesaid AMA-1 of Avian parasite *Eimeria*. A specific example of a DNA of the prevent invention is the one encoding the *Eimeria* AMA-1 comprising amino acid sequence shown in SEQ ID No. 2. More specifically, a DNA molecule of the present invention is that having a nucleotide sequence shown in SEQ ID No. 1.

However, the DNA of the present invention is not limited only to that having the sequence of SEQ ID No. 1, but includes a DNA encoding a protein that comprises the amino acid sequence modified by substitution, deletion, addition and/or insertion of one or more amino acids in SEQ ID No. 2, so long as the protein could induce the similar antibodies into chicken as those induced into chicken immunized with *Eimeria* AMA-1.

The numbers of the above amino acid modification are preferably, less than 10%, more preferably less than 5% to the whole of SEQ ID No. 2, and are most preferably less than 10 amino acids.

The DNA molecules encoding an antigenic protein of *Eimeria* AMA-1 of the present invention also include a DNA molecule that is hybridized to the DNA molecule of the open reading frame in SEQ ID No. 1 under high stringent condition. In this case, the high stringent condition is equivalent to "0.2×SSC and 68° C."

Moreover, the DNA molecules encoding an antigenic protein of *Eimeria* AMA-1 of the present invention include a DNA molecule encoding the protein having the amino acid sequence that is more than 90% (more preferably more than 95%) identity to the amino acid sequence shown in SEQ ID No. 2, and being antigenic protein of *Eimeria tenella* AMA-1. In this case, identity is calculated using Basic Local Alignment Search Tool (BLAST).

One of the methods to get the above DNA molecule that is hybridized to the DNA molecule of the open reading frame in SEQ ID No.1 under high stringent condition, or that is encoding the protein of amino acid sequence that is more than 90% identity to the amino acid sequence shown in SEQ ID No. 2 is modification to the DNA molecule of SEQ ID No. 1. To modify the DNA molecule, site-specific mutation using primer and/or random mutations are known in the art: see e.g.

Sambrook et al Chapter 13 of Molecular Cloning: A Laboratory Manual. 3rd Edition, Cold Spring Harbor Laboratory, Cold Spring Harbor, N.Y. 2001.

Vector and Construction of it

A DNA vector of the present invention is the vector containing the DNA molecule as described above. To get a DNA vector of the present invention, DNA having an artificial nucleotide sequence can be connected to the DNA molecule of the prevent invention. The sample of the DNA for connection is a linker used popularly in genetic engineering. The linker is at least one or two more nucleotide(s) that is/are not naturally connected to the DNA molecule of the present invention, and be appropriately designed depending on the site of the vector to be inserted.

The DNA vector in which the DNA molecule of the present invention is integrated can be chosen from a plasmid such as pBR322, pBR325, pUC7, pUC8, pUC18, pUC19, pBluescript or pGEM, a cosmid such as pHC79, or a phage such as λ or M13 phage. The vector is digested with appropriate restriction enzyme(s) and the DNA molecule of the present invention or other necessary DNA such as linker is inserted therein by the standard procedure.

A DNA vector to construct the expression vector for an antigenic protein of *Eimeria* AMA-1 is not limited, and may be chosen from the aforesaid vectors. A DNA vector to express the objective protein as a fusion protein with a Tag, by which the objective protein could be affinity-purified, is more suitable. For examples of such a vector, pGEX vector (AMERSHAM BIOSCIENCES Corp.) or pQE vector (QIAGEN Inc.) is commercially available. One example is pGEX-6p-3 described in EXAMPLE 3.

The transcriptional regulation region like a promoter or terminator is necessary to be included in the expression vector. The suitable promoter differs in host-by-host cell. For example, lac, tac or T5 promoter is used as promoter in the case of *E. coli* as host cell. OAX1 or GAPDH promoter in the case of Yeast, polyhedrin promoter in the case of insect cell, or cmv or β-actin promoter in the mammalian cells are suitable.

Host Cell

Using the resulting expression vector, a variety of host cells can be appropriately transformed to obtain a microorganism or cells capable of producing an antigenic protein of *Eimeria* AMA-1 or a recombinant protein comprising a part of SEQ ID No.2 and a Tag sequence.

Host cells used in herein can be chosen in terms of compatibility of the expression vector, suitability of the products, etc. and may be either prokaryotic or eukaryotic cells. Specific examples of the host cells include bacteria such as the genus *Escherichia* (e.g., *E. coli*) or the genus *Salmonella* (e.g., *Salmonella typhimurium*), and lower eukaryotic cells such as yeast (e.g., *Saccharomyces cerevisiae*) or fungi (e.g., *Penicillium*).

And examples of the host cells in higher eukaryotic cells are insect cells, Chinese hamster ovary (CHO) cells, CEF cells, or human cell lines (e.g., HeLa).

To transduce an expression vector said above into some host cells, appropriate methods well known to one skilled in the art according the host cells can be used.

Expression of an Antigenic Protein of Eimeria AMA-1

The host cells transformed with an appropriate expression vector can be cultured and proliferated under incubation conditions well known to one skilled in the art.

For example, the transformed *E. coli* can be well grown in LB medium at 37° C. under aerobic conditions. In producing an antigenic protein of *Eimeria* AMA-1, the condition for the induction of the protein can be chosen according to the used promoter. In the case of *E. coli* lactose promoter and operator system, as a specific example, it is achieved by adding an appropriate amount of isopropyl-1-thio-β-D-galactopyranoside (IPTG) to a culture medium.

A method to purify the antigenic protein of *Eimeria* AMA-1 is not particularly limited, but any known method is applicable to the purification in combination with techniques well known in this field. When the antigenic protein of *Eimeria* AMA-1 is expressed as a fusion protein containing some Tag that can be used in purification through an affinity column, the affinity column is a very convenient tool. For example, the antigenic protein of *Eimeria* AMA-1 expressed as fusion with glutathione S-transferase (GST) using pGEX vector could be purified easily through Glutathione Sepharose 4B column (AMERSHAM BIOSCIENCES Corp).

Vaccines Against Coccidiosis

Vaccines against coccidiosis of the present invention include DNA vaccine and protein vaccine. The DNA vaccine of the present invention can induce the immunity into chickens which are immunized with it. On the contrary, protein vaccine contains the antigenic protein of *Eimeria* AMA-1 of the present invention, which can induce the immunity into chickens.

The DNA vaccine of the present invention contains the DNA molecule of the present invention, and specifically can be as a main ingredient the recombinant DNA vector such as plasmid into which the DNA molecule of the present invention is inserted. The said recombinant DNA vector can be the expression vector for an antigenic protein of *Eimeria* AMA-1 said above, and is not limited only to it as far as the DNA vaccine can express the antigenic protein gene of *Eimeria* AMA-1 in the immunized chicken.

The DNA vaccine can contain any other ingredient besides the DNA molecule encoding the antigenic protein of *Eimeria* AMA-1. As the said other ingredient, CpG oligonucleotide, which is recognized by toll-like receptor on the cell surface and can activate cell-mediated immunity, or stabilizer additive can be used after being solubilized in the phosphate buffer saline (PBS).

The administration method of the DNA vaccine of the present invention is not particularly limited, and a general method of intramuscular, intravenous or subcutaneous injection is listed. The DNA vaccine is administered with 50 µl of 0.1 to 10 mg/ml, more preferably of 0.5 to 5 mg/ml per a bird.

The protein vaccine of the present invention consists chiefly of the antigenic protein of *Eimeria* AMA-1, and can contain any ingredients such as saline, adjuvant, and/or preservatives as long as the DNA vaccine can be safely immunized to chickens.

The administration method of the protein vaccine of the present invention is not particularly limited as far as it can induce immune responses to the administered chicken. It is preferable that the protein vaccine is injected with adjuvant, because it can induce strong immune responses to the injected chicken. Adjuvant can be selected among numerous ones well known in this art. For example, oil adjuvant or aluminum hydroxide. The amount of the injecting protein vaccine is not also limited. For example, protein suspended with PBS of more than 0.02 ml of more than 0.1 mg/ml can be injected, and in this case, the booster immunization is preferable.

BRIEF DESCRIPTION OF THE DRAWING FIGURES

FIG. 1 Results of tBLASTn search of *Eimeria* EST database using N-terminal amino acid sequence of PfAMA-1, in which BG725003 corresponds to SEQ ID NO: 16 and BG724708 corresponds to SEQ ID NO: 17

FIG. 2 Results of tBLASTn search of *Eimeria tenella* genome database using amino acid sequence of TgAMA-1. In FIGS. 2A-C, TgAMA1 corresponds to SEQ ID NO: 18 and c001002545 Contig 1 corresponds to SEQ ID NO: 19. In FIG. 2D, c008400755.Contig1, a genome sequence of *Eimeria tenella*, corresponds to SEQ ID NO: 20.

FIG. 4 Results of homology search using amino acid sequence of *Eimeria tenella* AMA-1, in which EtAMA1 corresponds to SEO ID NO: 2 and TgAMA1, the amino acid sequence of *Toxoplasma gondii* AMA-1 protein, corresponds to SEQ ID NO: 18.

LIST OF THE SEQ ID SEQUENCES

SEQ ID No. 1: cDNA Sequence of *Eimeria tenella* AMA-1gene

SEQ ID No. 2: Amino acid sequence of *Eimeria tenella* AMA-1 protein

SEQ ID No. 3: PCR primer BG708-F

SEQ ID No. 4: PCR primer BG003-R

SEQ ID No. 5: PCR primer BG003-F

SEQ ID No. 6: PCR primer c545-1F

SEQ ID No. 7: PCR primer c545-2R

SEQ ID No. 8: PCR primer c755-4F

SEQ ID No. 9: PCR primer c755-4R

SEQ ID No. 10: PCR Primer for site-specific mutagenesis EcoAMA1

SEQ ID No. 11: PCR Primer for site-specific mutagenesis AMA1Sal

SEQ ID No. 12: PCR Primer for site-specific mutagenesis XbaAMA1

SEQ ID No. 13: PCR Primer for site-specific mutagenesis AMA1endSal

SEQ ID No. 14: Oligonucleotide for adjuvant CpG

SEQ ID No. 15: Oligonucleotide for adjuvant CpG-30

DESCRIPTION OF THE PREFERRED EMBODIMENTS

The plasmid construction was essentially performed by the standard molecular biology techniques (Molecular Cloning: A Laboratory Manual. 3$^{rd}$ Edition, Cold Spring Harbor Laboratory, Cold Spring Harbor, N.Y. 2001). DNA restriction fragments were electrophoresed on agarose gels and purified with QIAquick Gel Extraction Kit (QIAGEN, Cat # 28704).

Polymerase chain reaction (PCR) was conducted, unless there is particular mention in the statement, using ExTaq polymerase (Product #: RR001A, TaKaRa Bio, Shiga, Japan) under the condition of 30 temperature cycles consisting of denaturation at 94° C. for 1 minute, annealing at 55° C. for 2 minute, and extention at 72° C. for 3 minute.

EXAMPLE 1

Cloning of cDNA Encoding *Eimeria* AMA-1

1.1 Preparation of *Eimeria Tenella* cDNA Library

Sporozoites were prepared from 1×10⁸ oocysts of Japanese field isolated strain of *Eimeria tenella* (sharing from Research Institute for Animal Science, Kanagawa, Japan) by the common procedure of this field, washed with PBS, and lysed with 0.5 ml of lysis buffer (4M guanidine thiocyanate, 25 mM sodium citrate, 0.5% sodium lauryl sarcosinate, and 0.1 M β-mercaptoethanol). Messenger RNA was purified on an oligo(dT) column (FastTrack 2.0 mRNA Isolation Kit, Invitrogen Carlsbad, Calif.) and used as a template for cDNA synthesis (cDNA Synthesis Kit, Product #: 6120, Takara Bio, Shiga, Japan). After double stranded cDNA synthesis, cDNA library was prepared using cDNA library Kit (Product #: 6119, TaKara Bio, Shiga, Japan) and cassette adapter in the kit.

1.2 Searching of *Eimeria* EST Database and Cloning 5' End of *Eimeria* AMA-1 Gene Malaria parasite, *Plasmodium falciparum* AMA-1 (PfAMA-1) gene and protein sequences had been published yet. *Eimeria* EST database was searched with translating BLAST (tBLASTn) tool (*E. tenella* OmniBlast of the Sanger Institute) using N-terminal 392 amino acid sequence of PfAMA-1 (Protein database Accession #: AAA29475), and resulted findings shown in FIG. 1.

High score EST sequences shown in FIG. 1A were aligned mutually. The results indicated that a part (394 bp) of BG725003 was identical to that of BG724708 as shown in FIG. 1B. Two PCR primers (BG708-F and BG003-R) were designed from the part before and after the identical region (underlined sequence in FIG. 1B). Sequences of these PCR primers were shown in SEQ ID No. 3 and 4, respectively. PCR was conducted using these PCR primers (BG708-F and BG003-R) and cDNA library described above as a template.

The PCR amplified a DNA fragment of about 0.6 kbp, which was ligated into the plasmid vector of PCR Script Amp cloning Kit (STRATAGENE, Product #: 211188). The resultant transformants were cultured and each plasmid was purified. The insert of each plasmid was sequenced, and a plasmid having the DNA fragment which encoded 5' non-translational region of 181 bp and N-terminal region (151 amino acids) of open reading frame (ORF) homologous to PfAMA-1 was found. The plasmid was named as pPCR-EtAMA1-N.

1.3 Cloning of Middle and 3'-End Regions of Sequence-Unknown *Eimeria* AMA-1

3' rapid amplification of cDNA end (3' RACE) was conducted using a new primer (BG003-F; SEQ ID No. 5) which existed in 3'-end of the insert of pPCR-EtAMA1-N, and the oligo (dT) primer being present in the cDNA Synthesis Kit described above (Takara Bio, Product #: 6120), but unfortunately no DNA was amplified. Therefore, as the next trial, *Eimeria* EST database was searched with translating BLAST (tBLASTn) tool (*E. tenella* OmniBlast of the Sanger Institute) using the amino acid sequence of 150$^{th}$ to 240$^{th}$ of *Toxoplasma gondii* AMA-1 (TgAMA-1) (Protein database Accession #: AAB65410), and consequently it was found that the amino acid sequence deduced from 753$^{rd}$ to 989$^{th}$ nucleotide sequence of c001002545.Contig1 was homologous to that of TgAMA-1 as shown in FIG. 2A.

Figure 2:
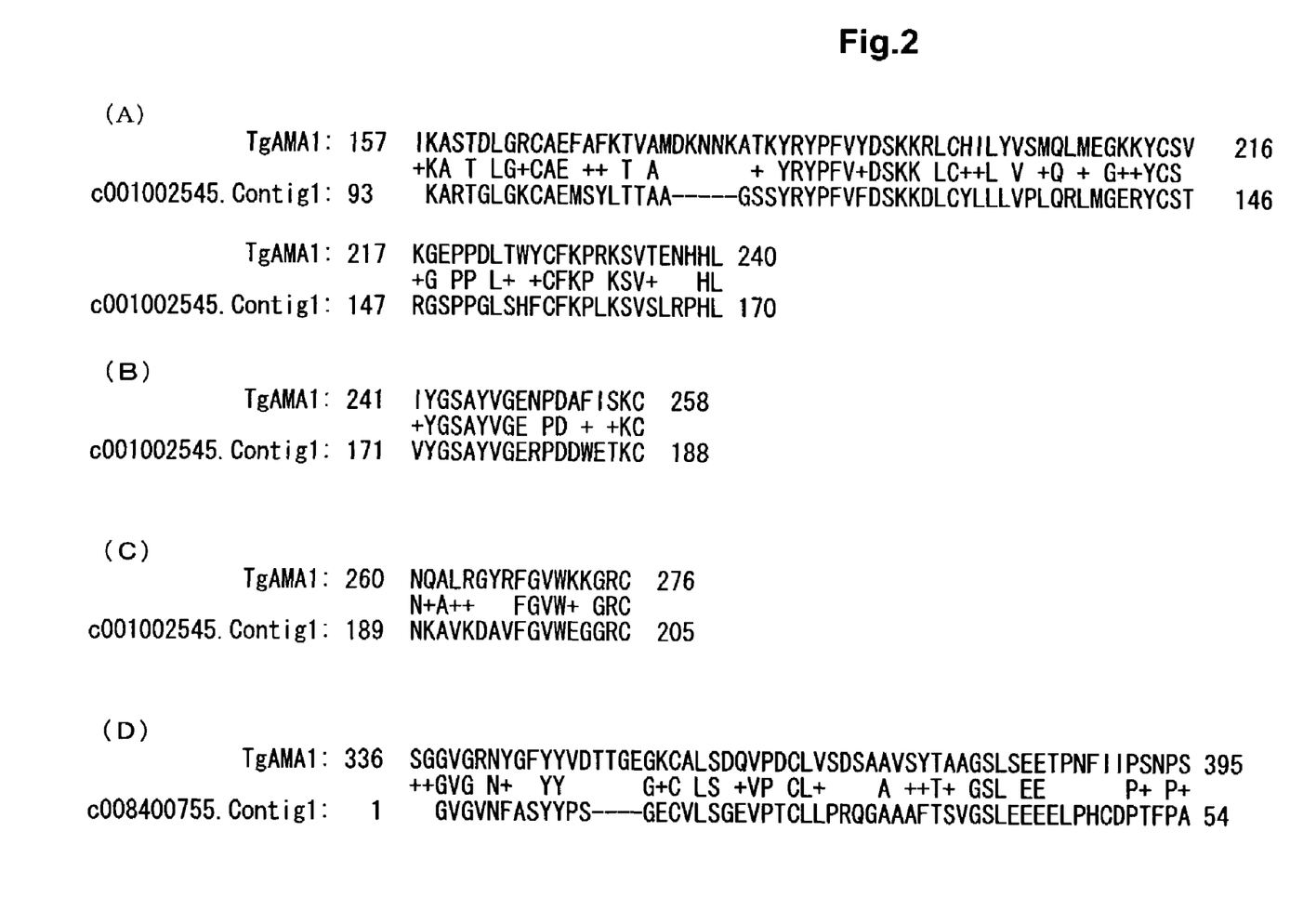

Furthermore *Eimeria* EST database was also searched with translating BLAST (tBLASTn) tool (http://www.sanger.ac.uk/cgi-bin/blast/submitblast/e_tenella/omni) using the amino acid sequence of 240th to 420th of TgAMA-1, and consequently it was found that the amino acid sequence deduced from 990th to 1046th nucleotide sequence of c001002545.Contig1 was homologous to that from 260$^{th}$ to 276th of TgAMA-1 as shown in FIG. 2B. The amino acid sequence from 260th to 276th of TgAMA-1 was found to be homologous to that deduced from 1255th to 1305th of c001002545.Contig1 as shown in FIG. 2C. Moreover, the amino acid sequence from 336th to 395th of TgAMA-1 was homologous to that deduced from 711st to 878th nucleotide sequence of c008400755.Contig1 as shown in FIG. 2D.

Figure 3A:
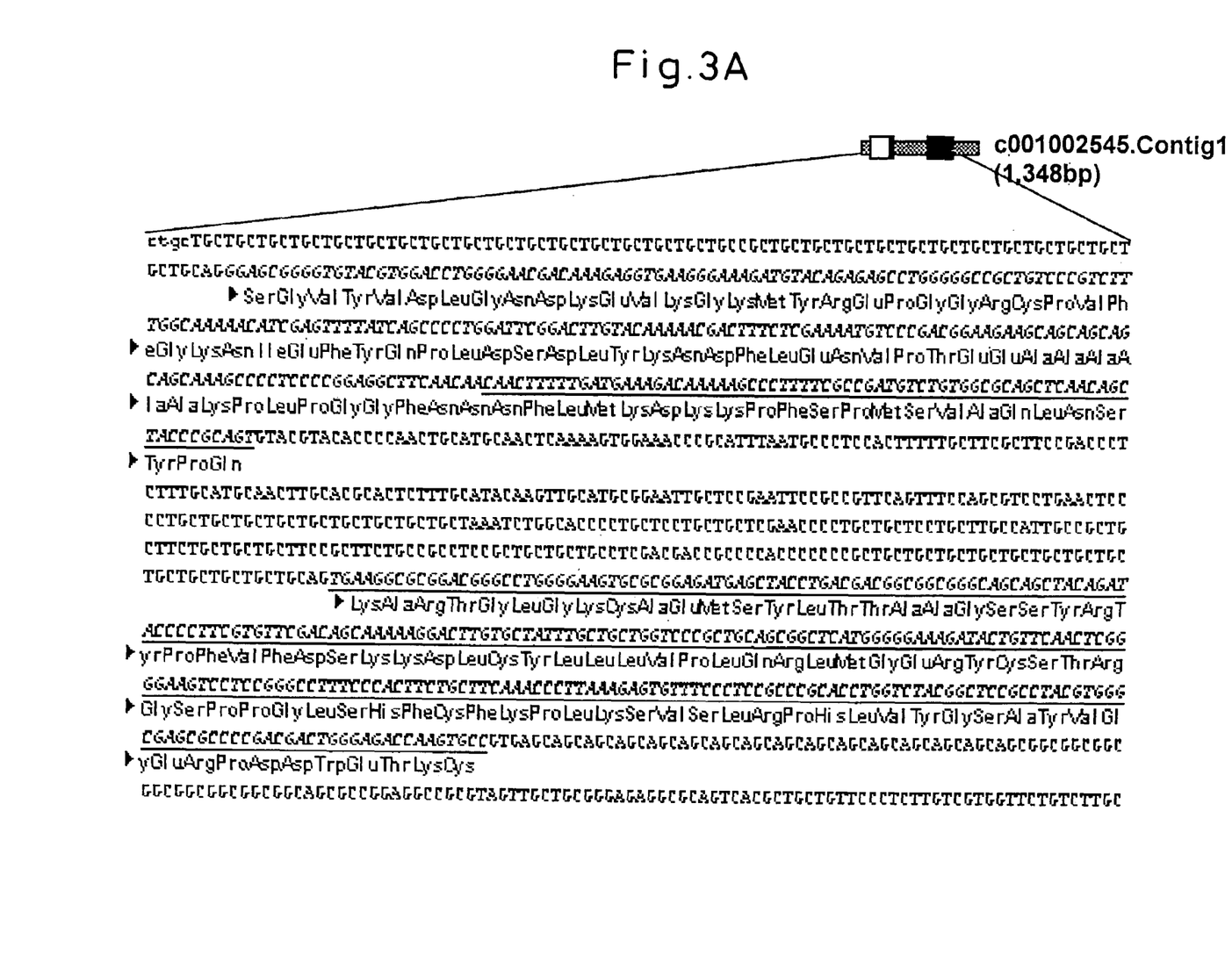
FIG. 3A illustrates portions of c001002545.Contig1, a sequence of the *Eimeria tenella* genome, and corresponds to nucleotides 1 to 1,196 of SEQ ID NO: 19.
Figure 3B:
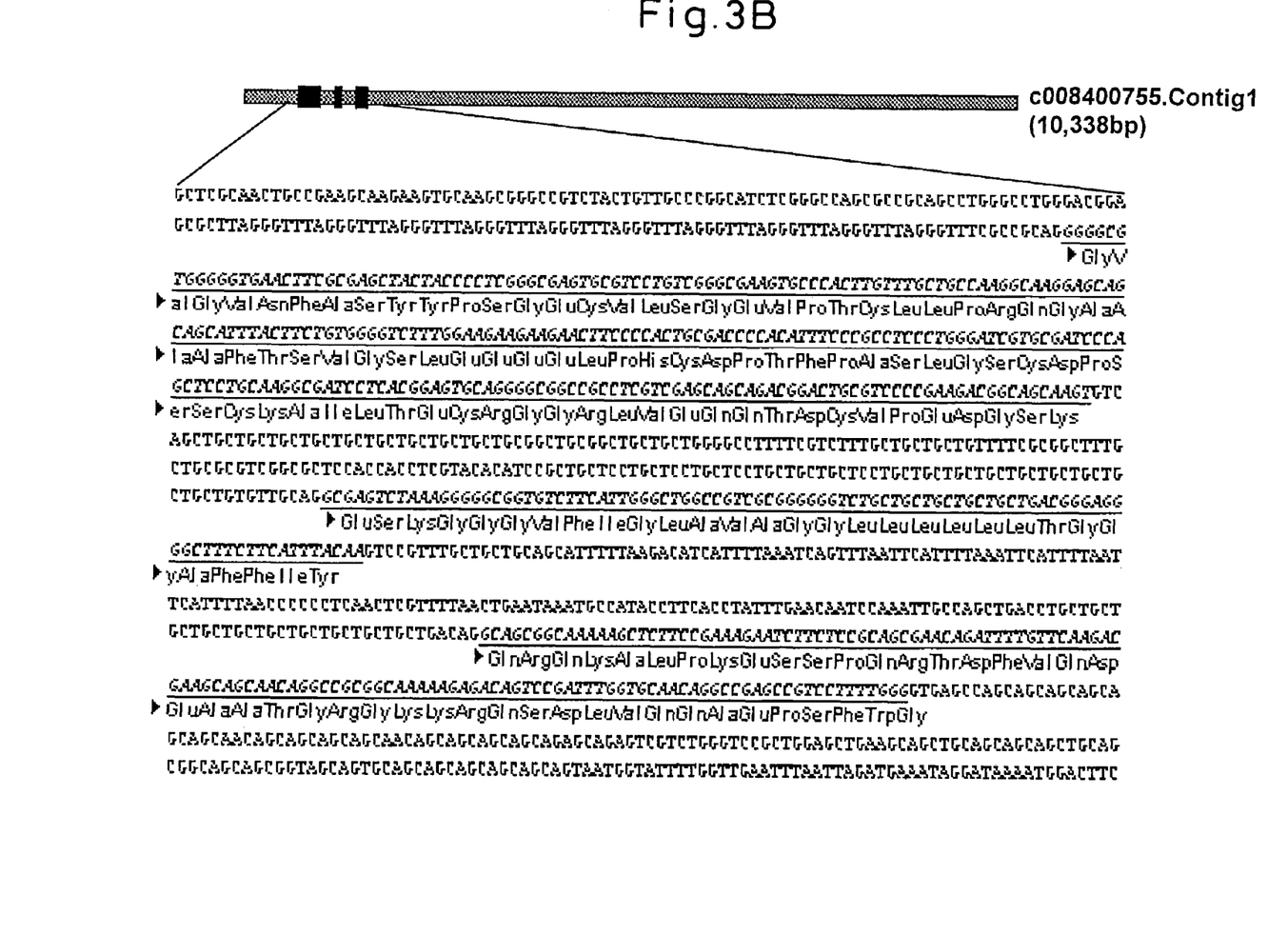
FIG. 3B illustrates c0008400755.Contig1, a genome sequence of *Eimeria tenella*, and corresponds to SEQ ID NO: 20.

Considering existence of intron from the above results and the rule of splicing signal, an exon-intron structure of *Eimeria* AMA-1 gene was presumed as shown in FIG. 3. From this presumption, four primers (c545-1F, c545-2R, c755-4F, c755-4R: Each sequence is SEQ ID No. 6 to 9, respectively) were designed.

PCR was conducted using cDNA library described in EXAMPLE 1.1 as a template, and PCR primer set of c545-1F and c545-2R. The DNA fragment of about 450 bp was amplified. In the case of PCR primer set of c545-1F and c755-4R, the DNA fragment of about 850 bp was amplified, inserted into pBluescript SK(+) plasmid vector (STRATAGENE, product #: 212205), and sequenced. As the inserted DNA seemed to encode a central region of *Eimeria* AMA-1, the plasmid was named as pBS-EtAMA1-M.

Next, 3' RACE was conducted using cDNA library described in EXAMPLE 1.1 as a template, a primer set of c755-4F and the oligodT primer in the cDNA Synthesis Kit described above (Takara Bio, Product #: 6120), and consequently a DNA fragment of about 630 bp was amplified. The DNA fragment was also inserted into pBluescript SK(+), and sequenced. The sequence data indicated that the insert was the DNA containing C-terminus region of *Eimeria* AMA-1 and 3' non-translational region. The inserted plasmid was named as pBS-EtAMA1-C.

The inserts of three plasmids, pPCR-EtAMA1-N, pBS-EtAMA1-M, and pBS-EtAMA1-C were 5'-terminus, center, and 3'-terminus of cDNA encoding *Eimeria tenella* AMA-1, respectively, from their sequence data. As three inserts had overlapping ends, where there were restriction enzyme sites, they were connected to one continuous cDNA (sequence of which is shown in SEQ ID No.1) using these sites. The plasmid containing the continuous cDNA was named as pBS-EtAMA1.

EXAMPLE 2

Nucleotide/Amino Acid Sequence Analysis of *Eimeria* AMA-1

The DNA molecule of SEQ ID No. 1 has total 2,002 nucleotides, which contain 5' non-translational region of 126 bp, one open reading frame of 536 amino acids, and 3' non-translational region including polyA signal. The amino acid sequence is shown in SEQ ID No. 2.

Protein-protein BLAST (BLASTp) search (*E. tenella* OmniBlast of the Sanger Institute) was conducted using the amino acid sequence shown in SEQ ID No. 2. No identical protein was found in Protein Data Bank, but the most similar protein was TgAMA-1 (E value of 9e-92 and 52% homology). The BLASTp search results were shown in FIG. 4. Outside of TgAMA-1, although the homology was less than 50%, several AMA-1 of *Plasmodium* species were hit as proteins having amino acid sequence homology to that of SEQ ID No. 2, which also strongly supports that the protein of SEQ ID No. 2 is *Eimeria* AMA-1. Up to current times, the nucleotide or amino acid sequence of *Eimeria* AMA-1 has not been published yet, and the sequence of this invention is the first report about full sequence data of *Eimeria* AMA-1.

From the amino acid sequence profile of SEQ ID No. 2, *Eimeria* AMA-1 includes a signal peptide at N-terminus (4th to 25th), and trans-membrane domain at the C-terminus (445th to 467th). Therefore it is guessed that this protein exists on the surface of *Eimeria* parasite and its C-terminus (from 468th to the end) is the cytoplasmic domain.

EXAMPLE 3

Production of Antigenic Protein of *Eimeria* AMA-1

3.1 Construction of an *E. coli* Expression Vector for *Eimeria* AMA-1

Figure 5:
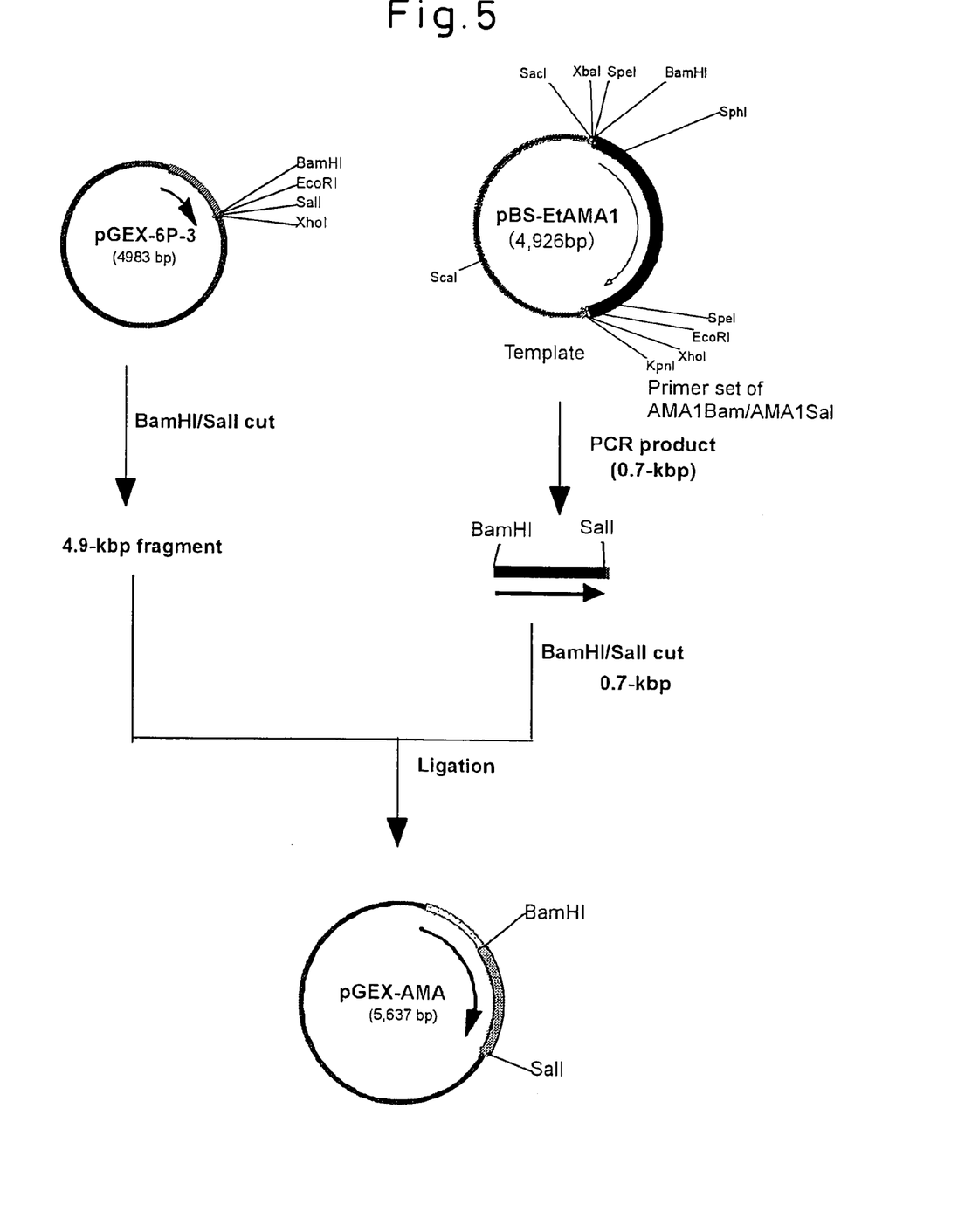
FIG. 5 Construction of the plasmid pGEX-EtAMA

To express an antigenic protein of *Eimeria* AMA-1 as a GST fusion protein, an *E. coli* expression vector pGEX-EtAMA was constructed as follows (FIG. 5). To ligate a DNA encoding *Eimeria* AMA-1 into a pGEX-6p-3 vector (AMERSHAM #27-4599-01) containing GST gene, a DNA fragment of about 1.1-kbp was amplified by PCR using pBS-EtAMA1 as a template, and EcoAMA1 (SEQ ID No. 10) and AMA1Sal (SEQ ID No. 11) as a set of primers.

The amplified DNA fragment was cut with EcoRI and SalI, fractionated by an agarose gel electrophoresis, and purified with QIAquick Gel Extraction Kit. Plasmid pGEX-6p-3 was also cut with EcoRI and SalI, fractionated by an agarose gel electrophoresis, and purified with QIAquick Gel Extraction Kit. These recovered DNA fragments were ligated to generate pGEX-EtAMA, and transferred into competent *E. coli* cells of JM109 (TaKaRa Bio Inc., Japan). The resulting ampicillin-resistant transformants were randomly picked up and cultured with each 2-ml LB broth containing ampicillin (LB+amp). Each plasmid was prepared by the standard (alkaline lysis) methods, and analyzed by restriction enzyme cutting. An objective plasmid selected by restriction enzyme analysis was sequenced with two sequence primers of AMERSHAM #27-1410-01 and 27-1411-01 to confirm that *Eimeria* AMA-1 gene was inserted in frame into the PGEX vector.

3.2 Expression of an Antigenic Protein of *Eimeria* AMA-1

*E. coli* BL21 cells (AMERSHAM #27-1542-01) were transformed with the pGEX-EtAMA. The resulting transformants were cultured with LB+amp broth for 16 hours, inoculated into fresh 100 volumes of LB+amp broth and continues to be culture for two hours. They were cultured for more three hours after adding IPTG to a final concentration of 1 mM, harvested by centrifugation, and lysed with Laemmli sample buffer (60 mM Tris-Cl (pH6.8), 25% glycerol, 2% SDS, 5% 2-mercaptoethanol, 0.01% bromphenol blue) by boiling at 100° C. The lysate was applied to 12.5% SDS-polyacrylamide gel electrophoresis (PAGE), and the gel was stained with 0.05% Coomassie brilliant blue (CBB) solution. The expected protein of about 53-kDa was induced very well as a GST-fusion protein.

3.3 Purification of an Antigenic Protein of *Eimeria* AMA-1

BL21 cells transformed with pGEX-GAPDH were cultured in a 2-ml LP+amp broth for 16 hours, and inoculated into fresh 100-ml LB+amp broth and continued culture for two hours. They were cultured for more three hours after adding IIPTG to a final concentration of 1 mM, harvested and wash with Phosphate buffer saline (PBS) twice. The cell pellet was suspended with Lysis buffer (50 mM Tris-Cl (pH8.0), 150 mM NaCl, 1 mM EDTA, 0.2 mM 4-2-aminoethyl)-benzenesulfonyl fluoride hydrochloride (Merck Ltd., Japan; product Name: Pefabloc SC), 1.5 mg/ml lysozyme), and shaken slowly for one hour and more 20 minutes followed by adding TRITON X-100, a non-ionic surfactant (octylphenoxypolyethoxyethanol), to a final concentration of 0.3%. The suspension was transferred to a tube and centrifuged at 12,000×g for 30 minutes. The pellet and supernatant were separated and applied to 12.5% SDS-PAGE. Most of fusion proteins were found in the pellet fraction.

The pellet was suspended with Laemmli sample buffer, boiled and applied to 8% SDS-PAGE. The objective fusion protein of 53-kDa was eluted and fractionated from the gel region in which the protein existed using Mini Whole Gel Eluter (Bio-Rad) with the elution buffer (60 mM Tris-Cl (pH 8.7), 25 mM boric acid). Recovered proteins in the fractions were checked by a 12.5% SDS-PAGE and CBB staining, and the fraction in which the objective protein existed and other proteins were not contaminated was selected. The antigenic protein of *Eimeria* AMA-1 of about 1 mg was purified from BL21 transformants cultivated with LB+amp broth of 100 ml as described herein.

EXAMPLE 4

Immune Response of Chickens Vaccinated with Antigenic Protein of *Eimeria* AMA-1

The antigenic protein of *Eimeria* AMA-1 (0.3 mg/ml) purified as described in the above Example 3 was mixed with equal volume of Freund's complete adjuvant (FCA; Sigma) to form 2 ml micelles. Ten chickens of 4 weeks old were subcutaneously immunized (sc) with each of 0.2 ml micelles, and boosted sc two times at intervals of a week with the same amount of AMA-1 protein and incomplete Freund's adjuvant (IFA; Sigma).

Ten days later after the last immunization, the immunized chickens were bled for about 2 ml each, and the peripheral blood lymphocytes and sera were prepared by the standard techniques. From five non-immunized chickens, the peripheral blood lymphocytes and sera were also prepared as negative control samples.

Antibodies in the sera against *E. tenella* sporozoites was checked by western blotting method. *E. tenella* of $1 \times 10^7$ sporozoites were lysed with Laemmli sample buffer and boiled for 5 min, and applied to 12.5% SDS-PAGE. After PAGE, proteins of sporozoites were blotted to a PVDF membrane (MILLIPORE; product name: Immobilon). After blotting, the membrane was dried and cut into total 12 pieces. Each piece was incubated with each serum (1:500 dilution) for 1 hour at room temperature (RT). After washing with PBS twice, the membrane was incubated with Goat anti-Chicken IgG (H+L) alkaline phosphatase conjugated (1:1,000 dilution; Bethyl, Inc. Catalog #A30-106AP) for 1 hour at RT, washed with PBS several times, and developed with the substrate solution of bromochloroindolyl phosphate/nitro blue tetrazolium (BCIP/NBT). All of 10 sera prepared from immunized chickens reacted specifically to about 60-kDa protein of sporozoites, while two negative control sera did not, although there were some proteins reacted nonspecifically. These results indicated that the antigenic protein of *Eimeria* AMA-1 could induce humoral immunity to chickens and the *Eimeria* AMA-1 of about 60-kDa is expressed in the *E. tenella* sporozoites.

EXAMPLE 5

Immune Responses of Chickens Injected with DNA Vaccine Containing *Eimeria* AMA-1 Gene The plasmid, pNZ45/46BacpA described in Examples of U.S. Pat. No. 6,764,684 was used as the backbone plasmid vector for DNA vaccine.

To get the DNA fragment containing restriction enzyme sites before and after the ORF of *Eimeria* AMA-1, PCR was conducted using pBS-EtAMA1 as the template, and primer set of XbaAMA1 (SEQ ID No. 12) and AMA1endSal (SEQ ID No. 13).

The amplified DNA of 1.6 kbp was cut with XbaI and SalI, and inserted into XbaI/SalI sites of pNZ45/46BacpA (7.4 kb). The resultant plasmid p45BacEtAMA1 (9 kbp) could be used as a DNA vaccine and/or a homologous vector for construction of recombinant herpes virus of turkey.

Next, to evaluate the plasmid for DNA vaccine, *Eimeria tenella* challenge to immunized chickens was conducted.

Fertilized SPF eggs of Line M were purchased from NIPPON INSTITUTE FOR BIOLOGICAL SCIENCE, Japan, and were hatched. The hatched chickens were divided into three groups. Plasmid p45BacEtAMA-1 of 1 mg and 0.1 mg each of adjuvant CpG (SEQ ID No. 14) and CpG-30 (SEQ ID No. 15) were diluted with 1 ml of PBS, and inoculated subcutaneously in the leg muscle of chickens of one group by in vivo electroporation (at 50V, 20 μsec three times and more three times at reverse polarity using Model ECM830; Gentronics Inc., Dan Diego, USA) twice at 2 and 9 days of age. Chickens of other two groups were not inoculated.

Four weeks later (at 37 days of age), body weights of all chickens were measured. Chickens except one of two non-immunized group were challenged orally (into maws of chickens) with 1,000 sporulated oocysts of *E. tenella* Rt7 strain (Japanese field isolated). Chickens not challenged were negative control (non-immunized and non-challenged). All chickens were observed until 8 days post challenge, and set up for measure of body weight. Feces were collected from 5 to 8 days post challenge, and fecal oocysts were checked by saturated saline floating method. When oocysts in feces were detected, fecal oocysts were counted microscopically after centrifugation in chromium sulfate solution, and calculated as number per gram-feces. The results of weight gains and discharged fecal oocyst numbers of each group are shown in Table 1.

Table 1 indicates that chickens immunized with DNA vaccine of this invention were statically different from non-immunized challenge control on both of discharged fecal oocyst number and weight gain, and that DNA vaccine could induce protective immunity against *Eimeria tenella* challenge.

TABLE 1

| Group | Number of birds | Evaluation Discharged fecal oocyst * | Weight gain (%) |
|---|---|---|---|
| Non-immunized, non-challenged control | 12 | – | 35.2 ± 3.8 |
| Non-immunized control | 10 | ++ | 17.9 ± 2.0 |
| Immunized with DNA vaccine | 10 | + | 30.0 ± 3.0 |

* Oocyst numbers per g-feces at 6 days post challenge:
(−) indicates under detectable ($10^3$);
(+) indicates less than $10^6$;
(++) indicates over $10^6$.

---

The invention claimed is:

1. An isolated DNA molecule encoding *Eimeria tenella* apical membrane antigen 1 comprising of the amino acid sequence of SEQ ID No: 2.

2. A DNA molecule encoding *Eimeria tenella* apical membrane antigen 1, wherein the DNA comprises of the nucleotide sequence of SEQ ID No: 1.

3. A DNA vector containing the DNA molecule as described in claim 1.

4. An isolated host cell having a DNA vector as described in claim 3.

5. A DNA vector containing a DNA molecule as described in claim 2.

6. An isolated host cell having a DNA vector as described in claim 5.

* * * * *

SEQUENCE LISTING

<160> NUMBER OF SEQ ID NOS: 15

<210> SEQ ID NO 1
<211> LENGTH: 2002
<212> TYPE: DNA
<213> ORGANISM: Eimeria tenella
<220> FEATURE:
<221> NAME/KEY: CDS
<222> LOCATION: (127)..(1737)
<223> OTHER INFORMATION:

<400> SEQUENCE: 1

```
tgcagcagca gcagctggcg tggcccttct gcagcagttg cggtctcttg atattccatt      60
cgagtttgat tttactcaaa atttgaaaaa aagaaatccc aaaacttgaa aagacccccc     120 agcacc atg cgg cgg ctt tcc cca gct ctg ggc ctt ctt gct gcg gcc        168
       Met Arg Arg Leu Ser Pro Ala Leu Gly Leu Leu Ala Ala Ala
       1               5                  10 ctc agc tgc gca ggg ccg gca gca ggg gtg cag cac aag ctg cag cac       216
Leu Ser Cys Ala Gly Pro Ala Ala Gly Val Gln His Lys Leu Gln His
15              20                  25                  30 agg cag cag cag cag cag cag cac agc cac gcc tca act tcg cat gct       264
Arg Gln Gln Gln Gln Gln Gln His Ser His Ala Ser Thr Ser His Ala
```

-continued

|  |  |  | 35 |  |  |  | 40 |  |  |  | 45 |  |  |  |
|---|---|---|---|---|---|---|---|---|---|---|---|---|---|---|
| gct | gca | gtt | ctt | gct | gct | tct | tcg | gat | gca | tcc | aca | gac | tcc | aat ccc | 312
| Ala | Ala | Val | Leu | Ala | Ala | Ser | Ser | Asp | Ala | Ser | Thr | Asp | Ser | Asn Pro |
|  |  |  | 50 |  |  |  | 55 |  |  |  | 60 |  |  |  |

| ttc | atg | cag | ccg | ccc | tat | gcc | gag | ttc | atg | gcc | gga | ttc | aac | att ccc | 360
| Phe | Met | Gln | Pro | Pro | Tyr | Ala | Glu | Phe | Met | Ala | Gly | Phe | Asn | Ile Pro |
|  | 65 |  |  |  |  | 70 |  |  |  |  | 75 |  |  |  |

| aaa | gtc | cac | ggg | agc | ggg | gtg | tac | gtg | gac | ctg | ggg | aac | gac | aaa gag | 408
| Lys | Val | His | Gly | Ser | Gly | Val | Tyr | Val | Asp | Leu | Gly | Asn | Asp | Lys Glu |
| 80 |  |  |  |  | 85 |  |  |  |  | 90 |  |  |  |  |

| gtg | aag | gga | aag | atg | tac | aga | gag | cct | ggg | ggc | cgc | tgt | ccc | gtc ttt | 456
| Val | Lys | Gly | Lys | Met | Tyr | Arg | Glu | Pro | Gly | Gly | Arg | Cys | Pro | Val Phe |
| 95 |  |  |  |  | 100 |  |  |  |  | 105 |  |  |  | 110 |

| ggc | aaa | aac | atc | gag | ttt | tat | cag | ccc | ctg | gat | tcg | gac | ttg | tac aaa | 504
| Gly | Lys | Asn | Ile | Glu | Phe | Tyr | Gln | Pro | Leu | Asp | Ser | Asp | Leu | Tyr Lys |
|  |  |  |  | 115 |  |  |  |  | 120 |  |  |  |  | 125 |

| aac | gac | ttt | ctc | gaa | aat | gtc | ccg | acg | gaa | gaa | gca | gca | gca | gca gca | 552
| Asn | Asp | Phe | Leu | Glu | Asn | Val | Pro | Thr | Glu | Glu | Ala | Ala | Ala | Ala Ala |
|  |  | 130 |  |  |  |  | 135 |  |  |  |  | 140 |  |  |

| aag | ccc | ctc | ccc | gga | ggc | ttc | aac | aac | aac | ttt | ttg | atg | aaa | gac aaa | 600
| Lys | Pro | Leu | Pro | Gly | Gly | Phe | Asn | Asn | Asn | Phe | Leu | Met | Lys | Asp Lys |
|  |  |  | 145 |  |  |  |  | 150 |  |  |  |  | 155 |  |

| aag | ccc | ttt | tcg | ccg | atg | tct | gtg | gcg | cag | ctc | aac | agc | tac | ccg cag | 648
| Lys | Pro | Phe | Ser | Pro | Met | Ser | Val | Ala | Gln | Leu | Asn | Ser | Tyr | Pro Gln |
| 160 |  |  |  |  | 165 |  |  |  |  | 170 |  |  |  |  |

| ttg | aag | gcg | cgg | acg | ggc | ctg | ggg | aag | tgc | gcg | gag | atg | agc | tac ctg | 696
| Leu | Lys | Ala | Arg | Thr | Gly | Leu | Gly | Lys | Cys | Ala | Glu | Met | Ser | Tyr Leu |
| 175 |  |  |  |  | 180 |  |  |  |  | 185 |  |  |  | 190 |

| acg | acg | gcg | gcg | ggc | agc | agc | tac | aga | tac | ccc | ttc | gtg | ttc | ggc agc | 744
| Thr | Thr | Ala | Ala | Gly | Ser | Ser | Tyr | Arg | Tyr | Pro | Phe | Val | Phe | Gly Ser |
|  |  |  |  | 195 |  |  |  |  | 200 |  |  |  |  | 205 |

| aaa | aag | gac | ttg | tgc | tat | ttg | ctg | ctg | gtc | ccg | ctg | cag | cgg | ctc atg | 792
| Lys | Lys | Asp | Leu | Cys | Tyr | Leu | Leu | Leu | Val | Pro | Leu | Gln | Arg | Leu Met |
|  |  |  | 210 |  |  |  |  | 215 |  |  |  |  | 220 |  |

| ggg | gaa | aga | tac | tgt | tca | act | cgg | gga | agt | cct | ccg | ggc | ctt | tcc cac | 840
| Gly | Glu | Arg | Tyr | Cys | Ser | Thr | Arg | Gly | Ser | Pro | Pro | Gly | Leu | Ser His |
|  |  | 225 |  |  |  |  | 230 |  |  |  |  | 235 |  |  |

| ttc | tgc | ttc | aaa | ccc | tta | aag | agt | gtt | tcc | ctc | cgc | ccg | cac | ctg gtc | 888
| Phe | Cys | Phe | Lys | Pro | Leu | Lys | Ser | Val | Ser | Leu | Arg | Pro | His | Leu Val |
|  | 240 |  |  |  |  | 245 |  |  |  |  | 250 |  |  |  |

| tac | ggc | tcc | gcc | tac | gtg | ggc | gag | cgc | ccc | gac | gac | tgg | gag | acc aag | 936
| Tyr | Gly | Ser | Ala | Tyr | Val | Gly | Glu | Arg | Pro | Asp | Asp | Trp | Glu | Thr Lys |
| 255 |  |  |  |  | 260 |  |  |  |  | 265 |  |  |  | 270 |

| tgc | ccg | aac | aag | gcg | gtg | aag | gac | gcg | gtg | ttc | ggg | gtg | tgg | gag ggg | 984
| Cys | Pro | Asn | Lys | Ala | Val | Lys | Asp | Ala | Val | Phe | Gly | Val | Trp | Glu Gly |
|  |  |  | 275 |  |  |  |  | 280 |  |  |  |  | 285 |  |

| ggc | cgc | tgc | gag | gag | cag | cgg | ctg | cgg | ctg | ggc | gcg | cag | act | gca gca | 1032
| Gly | Arg | Cys | Glu | Glu | Gln | Arg | Leu | Arg | Leu | Gly | Ala | Gln | Thr | Ala Ala |
|  |  | 290 |  |  |  |  | 295 |  |  |  |  | 300 |  |  |

| gca | gca | gca | aaa | gaa | gac | tgc | tgg | gct | ttg | gct | ttt | aat | aat | cct ttt | 1080
| Ala | Ala | Ala | Lys | Glu | Asp | Cys | Trp | Ala | Leu | Ala | Phe | Asn | Asn | Pro Phe |
|  |  | 305 |  |  |  |  | 310 |  |  |  |  | 315 |  |  |

| gct | gct | tcc | gac | cag | ccc | aca | tct | caa | gac | gaa | gca | gca | aca | agt ccc | 1128
| Ala | Ala | Ser | Asp | Gln | Pro | Thr | Ser | Gln | Asp | Glu | Ala | Ala | Thr | Ser Pro |
|  | 320 |  |  |  |  | 325 |  |  |  |  | 330 |  |  |  |

| ggc | tac | tac | ttc | cct | tcc | atc | acc | ccc | agc | cag | ccc | aaa | tcc | ggg ggc | 1176
| Gly | Tyr | Tyr | Phe | Pro | Ser | Ile | Thr | Pro | Ser | Gln | Pro | Lys | Ser | Gly Gly |
| 335 |  |  |  |  | 340 |  |  |  |  | 345 |  |  |  | 350 |

| gtg | ggg | gtg | aac | ttc | gcg | agc | tac | tac | ccc | tcg | ggc | gag | tgc | gtc ctg | 1224

```
                                                                                    -continued Val Gly Val Asn Phe Ala Ser Tyr Tyr Pro Ser Gly Glu Cys Val Leu
            355                 360                 365 tcg ggc gaa gtg ccc act tgt ttg ctg cca agg caa gga gca gca gca       1272
Ser Gly Glu Val Pro Thr Cys Leu Leu Pro Arg Gln Gly Ala Ala Ala
            370                 375                 380 ttt act tct gtg ggg tct ttg gaa gaa gaa gaa ctt ccc cac tgc gac       1320
Phe Thr Ser Val Gly Ser Leu Glu Glu Glu Glu Leu Pro His Cys Asp
        385                 390                 395 ccc aca ttt ccc gcc tcc ctg gga tcg tgc gat ccc agc tcc tgc aag       1368
Pro Thr Phe Pro Ala Ser Leu Gly Ser Cys Asp Pro Ser Ser Cys Lys
    400                 405                 410 gcg atc ctc acg gag tgc agg ggc ggc cgc ctc gtc gag cag cag acg       1416
Ala Ile Leu Thr Glu Cys Arg Gly Gly Arg Leu Val Glu Gln Gln Thr
415                 420                 425                 430 gac tgc gtc ccc gaa gac ggc agc aag tgc gag tct aaa ggg ggc ggt       1464
Asp Cys Val Pro Glu Asp Gly Ser Lys Cys Glu Ser Lys Gly Gly Gly
                435                 440                 445 gtc ttc att ggg ctg gcc gtc gcg ggg ggt ctg ctg ctg ctg ctg ctg       1512
Val Phe Ile Gly Leu Ala Val Ala Gly Gly Leu Leu Leu Leu Leu Leu
            450                 455                 460 acg gga ggg gct ttc ttc att tac aag cag cgg caa aaa gct ctt ccg       1560
Thr Gly Gly Ala Phe Phe Ile Tyr Lys Gln Arg Gln Lys Ala Leu Pro
        465                 470                 475 aaa gaa tct tct ccg cag cga aca gat ttt gtt caa gac gaa gca gca       1608
Lys Glu Ser Ser Pro Gln Arg Thr Asp Phe Val Gln Asp Glu Ala Ala
    480                 485                 490 aca ggc cgc ggc aaa aag aga cag tcc gat ttg gtg cag cag gcc gag       1656
Thr Gly Arg Gly Lys Lys Arg Gln Ser Asp Leu Val Gln Gln Ala Glu
495                 500                 505                 510 ccg tcc ttt tgg gaa gaa gca gaa gct gat gag cct cac gcc gat gaa       1704
Pro Ser Phe Trp Glu Glu Ala Glu Ala Asp Glu Pro His Ala Asp Glu
                515                 520                 525 aac acc caa gtg ctg ctg gac cag gaa tac tag tagcagcagc agcaacaaca    1757
Asn Thr Gln Val Leu Leu Asp Gln Glu Tyr
            530                 535 acagcagcag cagcagctac tgctgctgct gctgcagctg caggtgcagc tgcagcggca    1817
aaagagcagc aaagagcagc agcagcagca aagagcagca gcagcagcaa aaagcagcag    1877
cagcagcaaa agggaaattg aatttaactg aattcaattc gaattagttt cattcaaaag    1937
ttcttttctt caaattaact ctccattttc ctttttatt caaaaaaaaa aaaaaaaaa      1997 aaaaa                                                                 2002

<210> SEQ ID NO 2
<211> LENGTH: 536
<212> TYPE: PRT
<213> ORGANISM: Eimeria tenella

<400> SEQUENCE: 2

Met Arg Arg Leu Ser Pro Ala Leu Gly Leu Leu Ala Ala Ala Leu Ser
1               5                   10                  15

Cys Ala Gly Pro Ala Ala Gly Val Gln His Lys Leu Gln His Arg Gln
            20                  25                  30

Gln Gln Gln Gln Gln His Ser His Ala Ser Thr Ser His Ala Ala Ala
        35                  40                  45

Val Leu Ala Ala Ser Ser Asp Ala Ser Thr Asp Ser Asn Pro Phe Met
    50                  55                  60

Gln Pro Pro Tyr Ala Glu Phe Met Ala Gly Phe Asn Ile Pro Lys Val
65                  70                  75                  80
```

```
His Gly Ser Gly Val Tyr Val Asp Leu Gly Asn Asp Lys Glu Val Lys
                85                  90                  95

Gly Lys Met Tyr Arg Glu Pro Gly Gly Arg Cys Pro Val Phe Gly Lys
            100                 105                 110

Asn Ile Glu Phe Tyr Gln Pro Leu Asp Ser Asp Leu Tyr Lys Asn Asp
        115                 120                 125

Phe Leu Glu Asn Val Pro Thr Glu Glu Ala Ala Ala Ala Lys Pro
    130                 135                 140

Leu Pro Gly Gly Phe Asn Asn Asn Phe Leu Met Lys Asp Lys Lys Pro
145                 150                 155                 160

Phe Ser Pro Met Ser Val Ala Gln Leu Asn Ser Tyr Pro Gln Leu Lys
                165                 170                 175

Ala Arg Thr Gly Leu Gly Lys Cys Ala Glu Met Ser Tyr Leu Thr Thr
            180                 185                 190

Ala Ala Gly Ser Ser Tyr Arg Tyr Pro Phe Val Phe Gly Ser Lys Lys
            195                 200                 205

Asp Leu Cys Tyr Leu Leu Val Pro Leu Gln Arg Leu Met Gly Glu
    210                 215                 220

Arg Tyr Cys Ser Thr Arg Gly Ser Pro Pro Gly Leu Ser His Phe Cys
225                 230                 235                 240

Phe Lys Pro Leu Lys Ser Val Ser Leu Arg Pro His Leu Val Tyr Gly
                245                 250                 255

Ser Ala Tyr Val Gly Glu Arg Pro Asp Asp Trp Glu Thr Lys Cys Pro
            260                 265                 270

Asn Lys Ala Val Lys Asp Ala Val Phe Gly Val Trp Glu Gly Gly Arg
            275                 280                 285

Cys Glu Glu Gln Arg Leu Arg Leu Gly Ala Gln Thr Ala Ala Ala Ala
    290                 295                 300

Ala Lys Glu Asp Cys Trp Ala Leu Ala Phe Asn Asn Pro Phe Ala Ala
305                 310                 315                 320

Ser Asp Gln Pro Thr Ser Gln Asp Glu Ala Ala Thr Ser Pro Gly Tyr
                325                 330                 335

Tyr Phe Pro Ser Ile Thr Pro Ser Gln Pro Lys Ser Gly Gly Val Gly
            340                 345                 350

Val Asn Phe Ala Ser Tyr Tyr Pro Ser Gly Glu Cys Val Leu Ser Gly
            355                 360                 365

Glu Val Pro Thr Cys Leu Leu Pro Arg Gln Gly Ala Ala Ala Phe Thr
    370                 375                 380

Ser Val Gly Ser Leu Glu Glu Glu Leu Pro His Cys Asp Pro Thr
385                 390                 395                 400

Phe Pro Ala Ser Leu Gly Ser Cys Asp Pro Ser Ser Cys Lys Ala Ile
                405                 410                 415

Leu Thr Glu Cys Arg Gly Gly Arg Leu Val Glu Gln Thr Asp Cys
            420                 425                 430

Val Pro Glu Asp Gly Ser Lys Cys Glu Ser Lys Gly Gly Val Phe
    435                 440                 445

Ile Gly Leu Ala Val Ala Gly Gly Leu Leu Leu Leu Leu Thr Gly
    450                 455                 460

Gly Ala Phe Phe Ile Tyr Lys Gln Arg Gln Lys Ala Leu Pro Lys Glu
465                 470                 475                 480

Ser Ser Pro Gln Arg Thr Asp Phe Val Gln Asp Glu Ala Ala Thr Gly
                485                 490                 495
```

-continued

```
Arg Gly Lys Lys Arg Gln Ser Asp Leu Val Gln Gln Ala Glu Pro Ser
            500                 505                 510

Phe Trp Glu Glu Ala Glu Ala Asp Glu Pro His Ala Asp Glu Asn Thr
        515                 520                 525

Gln Val Leu Leu Asp Gln Glu Tyr
        530             535

<210> SEQ ID NO 3
<211> LENGTH: 22
<212> TYPE: DNA
<213> ORGANISM: Eimeria tenella

<400> SEQUENCE: 3
tgcagcagca gctggcgtgg cc                                              22

<210> SEQ ID NO 4
<211> LENGTH: 25
<212> TYPE: DNA
<213> ORGANISM: Eimeria tenella

<400> SEQUENCE: 4
gttgttgaag cctccgggga ggggc                                           25

<210> SEQ ID NO 5
<211> LENGTH: 27
<212> TYPE: DNA
<213> ORGANISM: Eimeria tenella

<400> SEQUENCE: 5
cccgacggaa gaagcagcag cagcagc                                         27

<210> SEQ ID NO 6
<211> LENGTH: 25
<212> TYPE: DNA
<213> ORGANISM: Eimeria tenella

<400> SEQUENCE: 6 gccccuccccc ggaggcttca acaac                                          25

<210> SEQ ID NO 7
<211> LENGTH: 26
<212> TYPE: DNA
<213> ORGANISM: Eimeria tenella

<400> SEQUENCE: 7
cacaccccga acaccgcgtc cttcac                                          26

<210> SEQ ID NO 8
<211> LENGTH: 28
<212> TYPE: DNA
<213> ORGANISM: Eimeria tenella

<400> SEQUENCE: 8
cctcacggag tgcaggggcg gccgcctc                                        28

<210> SEQ ID NO 9
<211> LENGTH: 28
<212> TYPE: DNA
<213> ORGANISM: Eimeria tenella

<400> SEQUENCE: 9
gaggcggccg cccctgcact ccgtgagg                                        28
```

```
<210> SEQ ID NO 10
<211> LENGTH: 27
<212> TYPE: DNA
<213> ORGANISM: Artificial Sequence
<220> FEATURE:
<223> OTHER INFORMATION: Primer for site-specific mutagenesis via PCR

<400> SEQUENCE: 10
gctgcttctt cgaattcatc cacagac                                       27

<210> SEQ ID NO 11
<211> LENGTH: 27
<212> TYPE: DNA
<213> ORGANISM: Artificial Sequence
<220> FEATURE:
<223> OTHER INFORMATION: Primer for site-specific mutagenesis via PCR

<400> SEQUENCE: 11
gtccgtctgc tggtcgacga ggcggcc                                       27

<210> SEQ ID NO 12
<211> LENGTH: 26
<212> TYPE: DNA
<213> ORGANISM: Artificial Sequence
<220> FEATURE:
<223> OTHER INFORMATION: Primer for site-ditrected mutagenesis via PCR

<400> SEQUENCE: 12
cccaaaactt gtctagaccc cccagc                                        26

<210> SEQ ID NO 13
<211> LENGTH: 29
<212> TYPE: DNA
<213> ORGANISM: Artificial Sequence
<220> FEATURE:
<223> OTHER INFORMATION: Primer for site-directed mutagenesis via PCR

<400> SEQUENCE: 13
ctgttgttgt cgactgctgc tgctactag                                     29

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide for adjuvant

<400> SEQUENCE: 14
tccatgacgt tcctgacgtt                                               20

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide for adjuvant

<400> SEQUENCE: 15
accgataacg ttgccggtgt cgttaccacg                                    30
```